(12) United States Patent
Buettelmann et al.

(10) Patent No.: US 7,091,222 B2
(45) Date of Patent: Aug. 15, 2006

(54) IMIDAZOLE DERIVATIVES

(75) Inventors: Bernd Buettelmann, Schopfheim (DE);
Simona Maria Ceccarelli, Basel (CH);
Georg Jaeschke, Basel (CH); Sabine Kolczewski, Rheinfelden (DE);
Richard Hugh Philip Porter, Reinach (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/874,948

(22) Filed: Jun. 23, 2004

(65) Prior Publication Data

US 2005/0009878 A1    Jan. 13, 2005

(30) Foreign Application Priority Data

Jul. 3, 2003    (EP) ................... 03014512

(51) Int. Cl.
*A61K 31/4439* (2006.01)
*C07D 401/06* (2006.01)

(52) U.S. Cl. ............... 514/341; 546/272.7; 546/272.4; 546/274.7; 546/275.1

(58) Field of Classification Search ............. 514/341; 546/272.7, 272.4, 274.7, 275.1
See application file for complete search history.

(56) References Cited

U.S. PATENT DOCUMENTS

2005/0143375 A1* 6/2005 Buettelmann et al. ... 514/227.5

FOREIGN PATENT DOCUMENTS

EP    0 304 910 A1    3/1989

OTHER PUBLICATIONS

Arena F. et al, Journal of Medicinal Chemistry, American Chemical Society, XP001005697, vol. 18, No. 11, pp. 1147-1150 (1975).
Sonogashira et al., Synthesis, pp. 777-778 (1977).
Cliff et al., Synthesis, 681, pp. 681-682 (1994).
Schlaeger et al., Cytotechnology, 30, pp. 71-83 (1999).
Porter et al., Br. J. Pharmacol., 128, pp. 13-20 (1999).

\* cited by examiner

*Primary Examiner*—Patricia L. Morris
(74) *Attorney, Agent, or Firm*—George W. Johnston; Patricia S. Rocha-Tramaloni; David E. Wildman

(57) ABSTRACT

The present invention relates to imidazole derivatives of the general formula

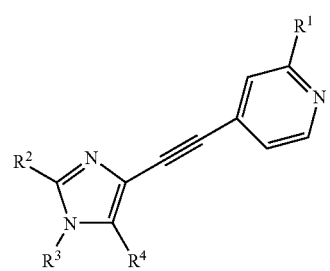

wherein $R^1$, $R^2$, $R^3$ and $R^4$ are as defined hereinabove. This invention also relates to the compound's pharmaceutically acceptable salt and processes for the preparation thereof. These compounds can be used for the manufacture of pharmaceutical compositions for the treatment and prevention of mGluR5 receptor mediated disorders. These compounds are useful, inter alia, in the treatment or prevention of acute and/or chronic neurological disorders such as psychosis, epilepsy, schizophrenia, Alzheimer's disease, cognitive disorders and memory deficit disorders, as well as chronic and acute pain.

11 Claims, No Drawings

IMIDAZOLE DERIVATIVES

FIELD OF THE INVENTION

The present invention relates to imidazole derivatives of the formula

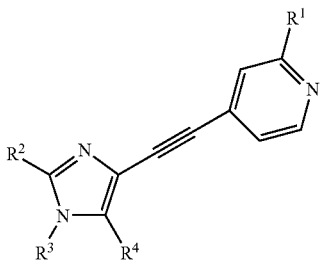

wherein $R^1$, $R^2$, $R^3$ and $R^4$ are as defined hereinbelow. This invention also relates to the compound's pharmaceutically acceptable salt and processes for the preparation thereof. These compounds can be used for the manufacture of pharmaceutical compositions for the treatment and prevention of mGluR5 receptor mediated disorders. These compounds are useful, inter alia, in the treatment or prevention of acute and/or chronic neurological disorders such as psychosis, epilepsy, schizophrenia, Alzheimer's disease, cognitive disorders and memory deficit disorders, as well as chronic and acute pain.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three groups:

mGluR1 and mGluR5 belong to group I; mGluR2 and mGluR3 belong to group II; and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)). Selective mGluR5 antagonists are especially useful for the treatment of anxiety and pain.

SUMMARY OF THE INVENTION

The invention relates to a compound of formula I

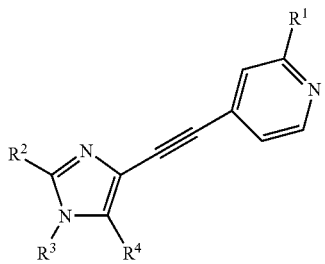

wherein $R^1$ is selected from halogen, lower alkyl, lower alkoxy, $CF_3$, $CF_2H$, $OCF_3$, $OCF_2H$, and cyano;

$R^2$ is lower alkyl or cycloalkyl;

$R^3$ is selected from lower alkyl, cycloalkyl, $-(CH_2)_n$-cycloalkyl, $-(CH_2)_n-CN$, $-(CH_2)_n-O$-lower alkyl, lower alkyleneoxy aryl, and $-R^5-F_n$, wherein $R^5$ is lower alkyl or lower alkenyl; and n is 1, 2 or 3; and $R^4$ is selected from hydrogen, C(O)H, and $CH_2R^5$, wherein $R^5$ is selected from hydrogen, OH, $C_1-C_6$-alkyl, and $C_3-C_{12}$-cycloalkyl;

or a pharmaceutically acceptable salt thereof, as well as to the above-mentioned compound as pharmaceutically active substances and their production.

Another embodiment of this invention relates to a process for preparing a compound according to formula I following the general procedures as outlined above for compounds of formula I.

Moreover, another embodiment of this invention relates to pharmaceutical compositions containing one or more compounds of the present invention and pharmaceutically acceptable excipients for the treatment and prevention of mGluR5 receptor mediated disorders, such as acute and/or chronic neurological disorders, in particular anxiety and chronic or acute pain.

Yet another embodiment of this invention also relates to the use of a compound in accordance with the present invention as well as its pharmaceutically acceptable salt for the manufacture of pharmaceutical compositions for the treatment and prevention of mGluR5 receptor mediated disorders as outlined above.

DETAILED DESCRIPTION OF THE INVENTION

The following definitions of general terms used in the present description apply irrespective of whether the terms in question appear alone or in combination.

The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "lower alkenyl" denotes straight-chain or branched hydrocarbon residues having from 2 to 10 carbon atoms, preferably with 2 to 6 carbon atoms and one or more olefinic double bond, preferably one olefinic double bond, such as vinyl, 1-propenyl, 2-propenyl (allyl) or 2-butenyl (crotyl).

The term "lower alkoxy" denotes an —O—$C_{1-6}$ alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers.

The term "aryl" denotes a monovalent aromatic carbocyclic radical consisting of one individual ring. Preferred aryl is phenyl.

The term "halogen" denotes fluorine, chlorine, bromine and iodine.

The term "cycloalkyl" denotes a saturated carbocyclic group, containing 3–6 carbon atoms.

The term "pharmaceutically acceptable salt" refers to any salt derived from an inorganic or organic acid or base.

One embodiment of the present invention is related to a compound of formula I

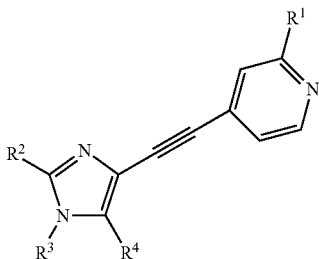

wherein
$R^1$ is selected from halogen, lower alkyl, lower alkoxy, $CF_3$, $CF_2H$, $OCF_3$, $OCF_2H$, and cyano;
$R^2$ is lower alkyl or cycloalkyl;
$R^3$ is selected from lower alkyl, cycloalkyl, —$(CH_2)_n$-cycloalkyl, —$(CH_2)_n$—CN, —$(CH_2)_n$—O-lower alkyl, lower alkyleneoxy aryl, and —$R^5$—$F_n$ wherein $R^5$ is lower alkyl or lower alkenyl; and n is 1, 2 or 3; and
$R^4$ is selected from hydrogen, C(O)H, and $CH_2R^5$, wherein $R^5$ is selected from hydrogen, OH, $C_1$–$C_6$-alkyl, and $C_3$–$C_{12}$-cycloalkyl;

or a pharmaceutically acceptable salt thereof.

Another embodiment of the present invention is related to a compound of formula I

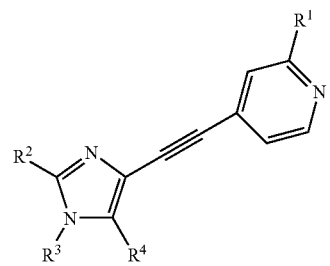

wherein
$R^1$ is selected from halogen and lower alkyl;
$R^2$ is lower alkyl or cycloalkyl;
$R^3$ is selected from lower alkyl, cycloalkyl, —$(CH_2)_n$-cycloalkyl, —$(CH_2)_n$—CN, —$(CH_2)_n$—O-lower alkyl, lower alkyleneoxy aryl, and —$R^5$—$F_n$ wherein $R^5$ is lower alkyl or lower alkenyl; and n is 1, 2 or 3; and
$R^4$ is selected from hydrogen and $CH_2R^5$, wherein $R^5$ is selected from hydrogen;

or a pharmaceutically acceptable salt thereof.

Another embodiment of the instant invention is the compounds of formula IA:

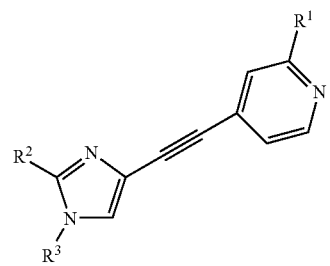

wherein
$R^1$ is selected from halogen, lower alkyl, lower alkoxy, $CF_3$, $CF_2H$, $OCF_3$, $OCF_2H$, and cyano;
$R^2$ is lower alkyl or cycloalkyl;
$R^3$ is selected from lower alkyl, cycloalkyl, —$(CH_2)_n$-cycloalkyl, —$(CH_2)_n$—CN, —$(CH_2)_n$—O-lower alkyl, lower alkyleneoxy aryl, and —$R^5$—$F_n$ wherein $R^5$ is lower alkyl or lower alkenyl; and n is 1, 2 or 3; as well as to a pharmaceutically acceptable salt thereof.

From the above, a preferred embodiment of the present invention is related to a compound of formula IA

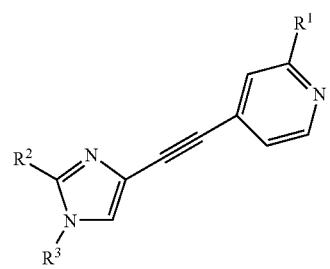

wherein

R$^1$ is selected from halogen and lower alkyl;

R$^2$ is lower alkyl or cycloalkyl; and

R$^3$ is selected from lower alkyl, cycloalkyl, —(CH$_2$)$_n$-cycloalkyl, —(CH$_2$)$_n$—CN, —(CH$_2$)$_n$—O-lower alkyl, lower alkyleneoxy aryl, and —R$^5$—F$_n$ wherein R$^5$ is lower alkyl or lower alkenyl; and n is 1, 2 or 3;

or a pharmaceutical acceptable salt thereof.

One embodiment of the compound of formula I in the present invention is where R$^1$ is lower alkyl; R$^2$ is lower alkyl; R$^3$ is lower alkyl; and R$^4$ is hydrogen.

Another embodiment of the compound of formula I in the present invention is where R$^1$ is lower alkyl; R$^2$ is lower alkyl; R$^3$ is cycloalkyl; and R$^4$ is hydrogen.

Another embodiment of the compound of formula I in the present invention is where R$^1$ is lower alkyl; R$^2$ is lower alkyl; R$^3$ is —(CH$_2$)$_n$—CN, where n is 1, 2, or 3; and R$^4$ is hydrogen.

Another embodiment of the compound of formula I in the present invention is where R$^1$ is lower alkyl; R$^2$ is lower alkyl; R$^3$ is —(CH$_2$)$_n$—O-lower alkyl, where n is 1, 2, or 3; and R$^4$ is hydrogen.

Another embodiment of the compound of formula I in the present invention is where R$^1$ is halogen; R$^2$ is lower alkyl; R$^3$ is lower alkyl; and R$^4$ is hydrogen.

Another embodiment of the compound of formula I in the present invention is where R$^1$ is halogen; R$^2$ is lower alkyl; R$^3$ is cycloalkyl; and R$^4$ is hydrogen.

Another embodiment of the compound of formula I in the present invention is where R$^1$ is lower alkyl; R$^2$ is lower alkyl; R$^3$ is lower lower alkyleneoxy aryl; and R$^4$ is hydrogen.

Another embodiment of the compound of formula I in the present invention is where R$^1$ is halogen; R$^2$ is cycloalkyl; R$^3$ is lower alkyl; and R$^4$ is hydrogen.

Another embodiment of the compound of formula I in the present invention is where R$^1$ is lower alkyl; R$^2$ is cycloalkyl; R$^3$ is lower alkyl; and R$^4$ is hydrogen.

Another embodiment of the compound of formula I in the present invention is where R$^1$ is lower alkyl; R$^2$ is lower alkyl; R$^3$ is —R$^5$—F$_n$, wherein R$^5$ is lower alkyl; and n is 1, 2 or 3; and R$^4$ is hydrogen.

Another embodiment of the compound of formula I in the present invention is where R$^1$ is halogen; R$^2$ is lower alkyl; R$^3$ is —R$^5$—F$_n$, wherein R$^5$ is lower alkyl; and n is 1, 2 or 3; and R$^4$ is hydrogen.

Another embodiment of the compound of formula I in the present invention is where R$^1$ is lower alkyl; R$^2$ is lower alkyl; R$^3$ is —R$^5$—F$_n$, wherein R$^5$ is lower alkenyl, and n is 1, 2 or 3; and R$^4$ is hydrogen.

Another embodiment of the compound of formula I in the present invention is where R$^1$ is halogen; R$^2$ is lower alkyl; R$^3$ is cycloalkyl; and R$^4$ is lower alkyl.

Another embodiment of the compound of formula I in the present invention is where R$^1$ is lower alkyl; R$^2$ is lower alkyl; R$^3$ is cycyloalkyl; and R$^4$ is lower alkyl.

A preferred embodiment is compounds above in which R$^3$ is —(CH$_2$)$_n$-cycloalkyl and the other definitions are as described above, for example the following compounds:

4-(1-cyclopropylmethyl-2-methyl-1H-imidazol-4-ylethynyl)-2-methyl-pyridine, 4-(1-cyclobutylmethyl-2-methyl-1H-imidazol-4-ylethynyl)-2-methyl-pyridine, 2-chloro-4-(1-cyclopropylmethyl-2-methyl-1H-imidazol-4-ylethynyl)-pyridine or 2-chloro-4-(1-cyclobutylmethyl-2-methyl-1H-imidazol-4-ylethynyl)-pyridine.

Another preferred embodiment is compounds, wherein R$^3$ is lower alkyl, for example the following compounds:

4-(1,2-dimethyl-1H-imidazol-4-ylethynyl)-2-methyl-pyridine, 4-(1-isopropyl-2-methyl-1H-imidazol-4-ylethynyl)-2-methyl-pyridine, 4-(1-isobutyl-2-methyl-1H-imidazol-4-ylethynyl)-2-methyl-pyridine or 2-chloro-4-(1-isobutyl-2-methyl-1H-imidazol-4-ylethynyl)-pyridine.

Yet another preferred embodiment is compounds, wherein R$^3$ is —CH$_2$—CN or —(CH$_2$)$_2$—O-lower alkyl, for example the following compounds:

[2-methyl-5-(2-methyl-pyridin-4-ylethynyl)-imidazol-1-yl]-acetonitrile or

4-[1-(2-methoxy-ethyl)-2-methyl-1H-imidazol-4-ylethynyl]-2-methyl-pyridine.

The compounds of formula I or IA of the invention may be prepared according to a process which comprises reacting a compound of formula II

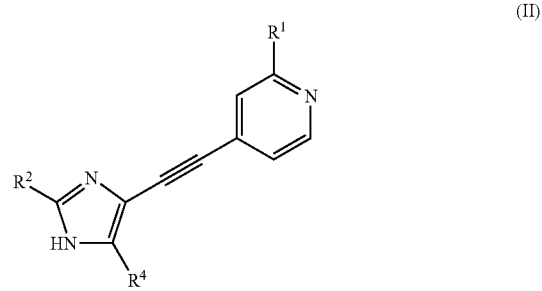

(II)

wherein R$^1$, R$^2$ and R$^4$ have the meanings as defined above, with a compound of formula III

R$^3$-Z    (III)

wherein R$^3$ has the meanings as defined above and Z is halogen or methylsulfonate (OSO$_2$CH$_3$).

The reaction as described above may be carried out in accordance with standard procedures, e.g. by heating a compound of formula II and a compound of formula III wherein Z is halogen with a base like sodium hydride in a solvent like tetrahydrofurane.

The compounds of formula I or IA of the invention may also be prepared according to a process which comprises reacting a compound of formula IV

(IV)

wherein $R^2$, $R^3$ and $R^4$ have the meanings as defined above, with a compound of formula V

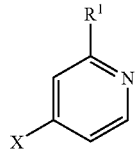
(V)

wherein $R^1$ has the meanings as defined above and X is halogen.

The reaction as described above may be carried out by a Sonogashira coupling of a compound of formula IV and a compound of formula V in the presence of, e.g., CuI, $(Ph_3P)_2PdCl_2$, $Et_3N$ in a solvent like tetrahydrofuran or dimethylformamide [Sonogashira et al., Synthesis 777 (1977)]. In one embodiment the meaning X in compounds of formula V is bromine or iodine.

The compounds of formula I or IA of the invention may be prepared according to a process which comprises reacting a compound of formula VI

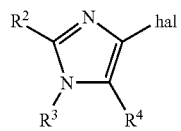
(VI)

wherein $R^2$, $R^3$ and $R^4$ have the meanings as defined above and hal is halogen, with compound of formula VII

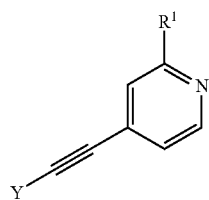
(VII)

wherein $R^1$ has the meaning as defined above and Y is trimethylsilyl or hydrogen.

The reaction as described above may, e.g. be carried out in the presence of CuI, $(Ph_3P)_2PdCl_2$, $Et_3N$, $n-Bu_4F$ in a solvent like tetrahydrofuran or dimethylformamide.

If desired, each of the above compounds obtained may be converted into their pharmaceutically acceptable salts.

The salt forms are made by standard procedures known to the skilled artisan.

The compounds of formulae III and V are commercially available or their preparation is known to the skilled artisan.

The compounds of general formula I and their pharmaceutically acceptable salts can also be manufactured by the procedure, as shown by reacting a compound of formula

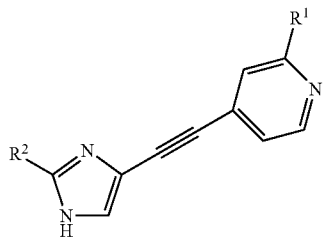
II with a compound of formula $R^3$-Z     III wherein $R^3$ has the meanings as defined above and Z is halogen, compound of formula

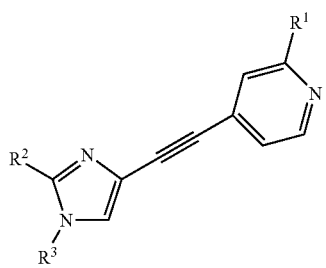
IA wherein $R^1$, $R^2$ and $R^3$ are as described above and Hal is preferably chloro, bromo or iodo, and if desired, when $R^4$ is other than hydrogen, The compounds of general formula I and their pharmaceutically acceptable salts can also be manufactured by the general procedure, as shown by reacting the compound of formula IA with a compound of formula:

$R^4$Hal     VI to compound of formula

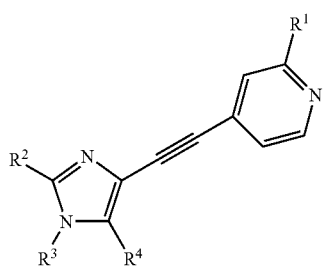
I wherein $R^1$, $R^2$, $R^3$ and $R^4$ are as described above.

If desired, each of the compounds obtained above may be converted into pharmaceutically acceptable salts.

The compounds can be synthesized by the procedure shown in the following schemes:
Scheme 1
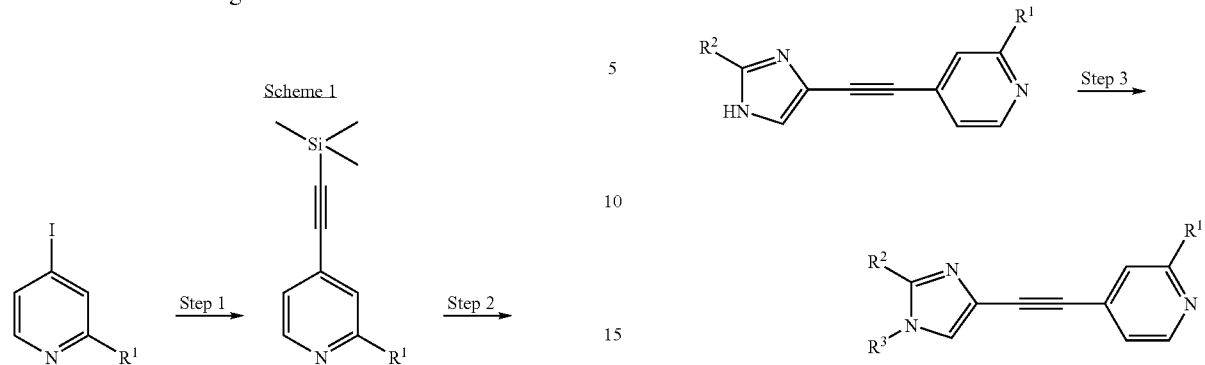
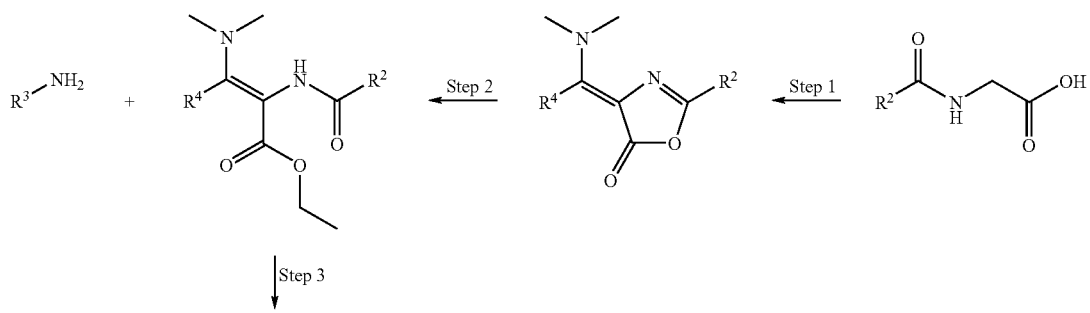
Scheme 2
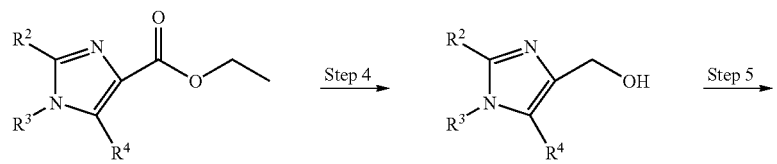
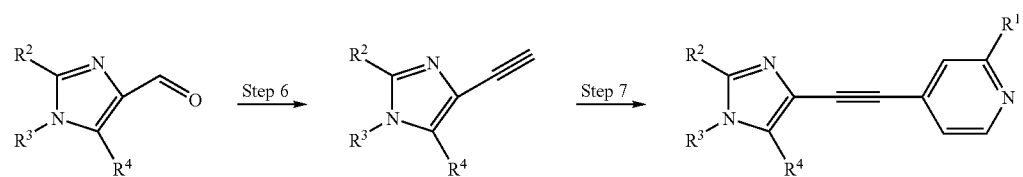

Scheme 3

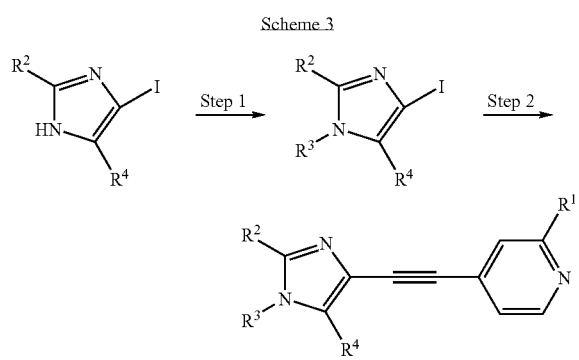

wherein the definitions are as described above.

The above scheme 1 is described in more detail with respect to the preparation of the compound, wherein $R^1$ is chloro, $R^2$ is methyl and $R^3$ is isobutyl.

Step 1

2-Chloro-4-iodo-pyridine is dissolved in THF and triethyl amine. This mixture is evacuated and backfilled with argon several times to remove oxygen from the solution.

Triphenylphosphine and bis(triphenylphosphine)palladium(II)chloride are added and the reaction mixture is stirred at room temperature for about 1 h. Copper(I)iodide and trimethylsilylacetylene are added. The reaction mixture is stirred at room temperature overnight and worked-up in usual manner. The desired product is used without any further purification for the next step.

Step 2

Solution 1: 2-Chloro-4-trimethylsilanylethynyl-pyridine as indicated in step 1) and 5-iodo-2-methyl-1H-imidazole, (synthesis: M. D. Cliff, S. G. Pyne, *Synthesis* 1994, 681–682) are dissolved in THF and DMF. This mixture is evacuated and backfilled with argon several times to remove oxygen from the solution.

Solution 2: Triphenylphosphine, bis(triphenylphosphine)-palladium(II)chloride, copper(I)iodide and triethyl amine are dissolved in THF. This mixture is also evacuated and backfilled with argon several times to remove oxygen from the solution.

Solution 2 is heated to about 40° C. and solution 1 is added dropwise. The reaction mixture is heated to about 60° C. and tetrabutylammonium fluoride solution is added dropwise during 45 min. The reaction is than stirred at room temperature overnight. The solvent is evaporated. The residue is worked-up and purified in conventional manner.

Step 3

Sodium hydride is suspended in THF. A solution of 2-chloro-4-(2-methyl-1H-imidazol-4-ylethynyl)-pyridine in THF is added and the reaction mixture is stirred at room temperature for about 30 min. A solution of isobutylbromide in THF is added and stirring is continued overnight. The product is isolated and purified in conventional manner.

If in accordance with the above scheme a mixture of two regioisomers is obtained for the final products, this mixture can be separated on a HPLC (chiralpak AD, heptane/ethanol 4/1).

The above scheme 2 is described in more detail with respect to the preparation of the compound, wherein $R^1$ is chloro, $R^2$ is methyl, $R^3$ is cyclopropyl and $R^4$ is methyl.

Step 1

N-Acetylglycine and Phosphoroxychloride are mixed and cooled to 5° C. N',N-Dimethylacetamide is added drop-wise slowly during 30 min at 5–10° C. (exothermic!). The reaction mixture is stirred at 45° C. for 2.5 hrs and then cooled to room temperature. Dichloromethane is added and the mixture poured into ice-water. The mixture, which is adjusted to pH 8 with ammonium hydroxide, was worked-up and purified in conventional manner.

Step 2

4-[1-Dimethylamino-eth-(Z)-ylidene]-2-methyl-4H-oxazol-5-one is dissolved in ethanol and sodium hydride is added at room temperature. The dark solution is refluxed for 1 h. The solvent is evaporated and the crude product is used without any further purification for the next step.

Step 3

(Z)-2-Acetylamino-3-dimethylamino-but-2-enoic acid ethyl ester and cyclopropylamine are stirred at room temperature in acetic acid for 2 hrs. The reaction mixture is diluted slowly with water and evaporated under vacuum at 35° C. Water is added to the residue and evaporated again at 35° C. The same procedure is repeated twice with toluene to obtain a crude intermediate, which was refluxed together with fine powdered ammonium sulfate in hexamethyldisilazane over night at 145° C. The reaction mixture is worked-up and purified in conventional manner.

Step 4

Cyclopropyl-2,5-dimethyl-1H-imidazole-4-carboxylic acid ethyl ester is dissolved in dry THF and cooled to 0° C. Lithium aluminum hydride is added drop wise and stirred for 1 h at 0° C. The reaction mixture is quenched and worked-up in usual manner. The desired product is used without any further purification for the next step.

Step 5

Cyclopropyl-2,5-dimethyl-1H-imidazol-4-yl)-methanol is dissolved in dichloromethane. Mangan (IV) oxid is added and the reaction mixture stirred at reflux for 2 hrs. The suspension is filtered through a dicalite speed plus pad and evaporated to obtain the desired product.

Step 6

Diazo-2-oxo-propyl)-phosphonic acid dimethyl ester is dissolved in methanol. Potassium carbonate is added. A solution of 1-Cyclopropyl-2,5-dimethyl-1H-imidazole-4-carbaldehyde in methanol is added drop wise at room temperature. The reaction mixture is stirred at room temperature overnight, worked-up and purified in conventional manner.

Step 7

2-Chloro-4-iodo-pyridine is dissolved in THF and triethyl amine. This mixture is evacuated and backfilled with argon several times to remove oxygen from the solution. Triphenylphosphine and bis(triphenylphosphine)palladium(II) chloride are added and the reaction mixture is stirred at room temperature for about 1 h. Copper(I)iodide and 1-cyclopropyl-4-ethynyl-2,5-dimethyl-1H-imidazole are added. The reaction mixture is stirred at room temperature overnight, worked-up and purified in conventional manner.

The above scheme 3 is described in more detail with respect to the preparation of the compound, wherein $R^1$ is chloro, $R^2$ is methyl, $R^3$ is 1,1-difluoroethyl and $R^4$ is hydrogen.

Step 1

Sodium hydride is suspended in THF. A solution of 5-iodo-2-methyl-1H-imidazole (synthesis: M. D. Cliff, S. G. Pyne, Synthesis 1994, 681–682) in THF is added and the reaction mixture is stirred at room temperature for about 30 min. A solution of 2-bromo-1,1-difluoroethane in THF is added and stirring is continued overnight. The product is isolated and purified in conventional manner.

If in accordance with the above scheme a mixture of two regioisomers is obtained for the final products, this mixture can be separated by HPLC (chiralpak AD, heptane/ethanol 4/1).

Step 2

Solution 1: 2-Chloro-4-trimethylsilanylethynyl-pyridine and 1-(2,2-difluoro-ethyl)-4-iodo-2-methyl-1H-imidazole are dissolved in THF and DMF. This mixture is evacuated and backfilled with argon several times to remove oxygen from the solution.

Solution 2: Triphenylphosphine, bis(triphenylphosphine)-palladium(II)chloride, copper(I)iodide and triethyl amine are dissolved in THF. This mixture is also evacuated and backfilled with argon several times to remove oxygen from the solution.

Solution 2 is heated to about 40° C. and solution 1 is added dropwise. The reaction mixture is heated to about 60° C. and tetrabutylammonium fluoride solution is added dropwise during 45 min. The reaction is then stirred at room temperature overnight. The solvent is evaporated. The residue is worked-up and purified in conventional manner.

Pharmaceutically acceptable salts of compounds of formula I can be manufactured readily according to methods known in the art and taking into consideration the nature of the compound to be converted into a salt. Inorganic or organic acids such as, for example, hydrochloric acid, hydrobromic acid, sulfuric acid, nitric acid, phosphoric acid or citric acid, formic acid, fumaric acid, maleic acid, acetic acid, succinic acid, tartaric acid, methanesulfonic acid, p-toluenesulfonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method:

For binding experiments, cDNA encoding human mGlu 5a receptor was transiently transfected into EBNA cells using a procedure described by Schlaeger and Christensen [Cytotechnology 15:1–13 (1998)]. Cell membrane homogenates were stored at −80° C. until the day of assay where upon they were thawed and resuspended and polytronised in 15 mM Tris-HCl, 120 mM NaCl, 100 mM KCl, 25 mM $CaCl_2$, 25 mM $MgCl_2$ binding buffer at pH 7.4 to a final assay concentration of 20 μg protein/well.

Saturation isotherms were determined by addition of twelve [$^3$H]MPEP concentrations (0.04–100 nM) to these membranes (in a total volume of 200 μl) for 1 h at 4° C. Competition experiments were performed with a fixed concentration of [$^3$H]MPEP (2 nM) and $IC_{50}$ values of test compounds evaluated using 11 concentrations (0.3–10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 μM MPEP. The radioactivity on the filter was counted (3 min) on a Packard Top-count microplate scintillation counter with quenching correction after addition of 45 μl of microscint 40 (Canberra Packard S. A., Zürich, Switzerland) and shaking for 20 min.

For functional assays, [$Ca^{2+}$]i measurements were performed as described previously by Porter et al. [Br. J. Pharmacol. 128:13–20 (1999)] on recombinant human mGlu 5a receptors in HEK-293 cells. The cells were dye loaded using Fluo 4-AM (obtainable by FLUKA, 0.2 μM final concentration). [$Ca^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving $IC_{50}$, and Hill coefficient using an iterative non linear curve fitting software (Xcel fit).

For binding experiments the Ki values of the compounds tested are given. the Ki value is defined by the following formula:

$$K_i = IC_{50}/[1 + L/K_d]$$

in which the $IC_{50}$ values are those concentrations of the compounds tested which cause 50% inhibition of the competing radioligand ([$^3$H]MPEP). L is the concentraion of radioligand used in the binding experiment and the $K_d$ value of the radioligand is empirically determined for each batch of membranes prepared.

The compounds of the present invention are mGluR 5a receptor antagonists. The activities of compounds of formula I as measured in the assay described above are in the range of $K_i$<200 nM.

| Example No. | Ki (nM) |
|---|---|
| 2 | 68 |
| 4 | 38 |
| 6 | 33 |
| 7 | 122 |
| 8 | 191 |
| 12 | 49 |
| 13 | 28 |
| 21 | 54 |
| 22 | 95 |

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided to further elucidate the invention:

EXAMPLE 1

4-(1,2-Dimethyl-1H-imidazol-4-ylethynyl)-2-methyl-pyridine

Sodium hydride (76 mg, 55%, 1.57 mmol) was suspended in 2 mL of dry THF. A solution of 2-methyl-4-(2-methyl-1H-imidazol-4-ylethynyl)-pyridine (150 mg, 0.76 mmol) in 8 mL of dry THF was added and the reaction mixture was stirred at room temperature for 30 min. A solution of methyliodide (142 mg, 1.00 mmol) in 1 mL of dry THF was added and stirring was continued overnight. The reaction mixture was poured into 70 mL of water and extracted three times with ethyl acetate (70 mL each). The combined organic extracts were dried with sodium sulfate, filtered and evaporated. The crude product was purified by flash chromatography on silica gel (dichloromethane/methanol 100:0->90:10 gradient) and a mixture of two regioisomers was obtained. This mixture could be separated by HPLC (chiralpak AD, heptane/ethanol 4/1) and the desired compound was obtained as a white solid (40 mg, 25%), MS: m/e=212.2 (M+H$^+$).

EXAMPLE 2

4-(1-Isopropyl-2-methyl-1H-imidazol-4-ylethynyl)-2-methyl-pyridine

The title compound, MS: m/e=240.3 (M+H$^+$), was prepared in accordance with the general method of example 1 from 2-methyl-4-(2-methyl-1H-imidazol-4-ylethynyl)-pyridine and isopropylbromide.

EXAMPLE 3

4-(1-Isobutyl-2-methyl-1H-imidazol-4-ylethynyl)-2-methyl-pyridine

The title compound, MS: m/e=254.2 (M+H$^+$), was prepared in accordance with the general method of example 1 from 2-methyl-4-(2-methyl-1H-imidazol-4-ylethynyl)-pyridine and isobutylbromide.

EXAMPLE 4

4-(1-Cyclopropylmethyl-2-methyl-1H-imidazol-4-ylethynyl)-2-methyl-pyridine

The title compound, MS: m/e=252.1 (M+H$^+$), was prepared in accordance with the general method of example 1 from 2-methyl-4-(2-methyl-1H-imidazol-4-ylethynyl)-pyridine and bromomethyl-cyclopropane.

EXAMPLE 5

4-(1-Cyclobutylmethyl-2-methyl-1H-imidazol-4-ylethynyl)-2-methyl-pyridine

The title compound, MS: m/e=266.2 (M+H$^+$), was prepared in accordance with the general method of example 1 from 2-methyl-4-(2-methyl-1H-imidazol-4-ylethynyl)-pyridine and bromomethyl-cyclobutane.

EXAMPLE 6

[2-Methyl-4-(2-methyl-pyridin-4-ylethynyl)-imidazol-1-yl]-acetonitrile

The title compound, MS: m/e=237.2 (M+H$^+$), was prepared in accordance with the general method of example 1 from 2-methyl-4-(2-methyl-1H-imidazol-4-ylethynyl)-pyridine and bromoacetonitrile.

EXAMPLE 7

4-[1-(2-Methoxy-ethyl)-2-methyl-1H-imidazol-4-ylethynyl]-2-methyl-pyridine

The title compound, MS: m/e=256.2 (M+H$^+$), was prepared in accordance with the general method of example 1 from 2-methyl-4-(2-methyl-1H-imidazol-4-ylethynyl)-pyridine and 2-bromoethyl-methylether.

EXAMPLE 8

2-Chloro-4-(1-isobutyl-2-methyl-1H-imidazol-4-ylethynyl)-pyridine

The title compound, MS: m/e=274.1 (M+H$^+$), was prepared in accordance with the general method of example 1 from 2-chloro-4-(2-methyl-1H-imidazol-4-ylethynyl)-pyridine and 1-bromo-2-methylpropane.

EXAMPLE 9

2-Chloro-4-(1-cyclopropylmethyl-2-methyl-1H-imidazol-4-ylethynyl)-pyridine

The title compound, MS: m/e=272.2 (M+H$^+$), was prepared in accordance with the general method of example 1 from 2-chloro-4-(2-methyl-1H-imidazol-4-ylethynyl)-pyridine and bromomethyl-cyclopropane.

EXAMPLE 10

2-Chloro-4-(1-cydobutylmethyl-2-methyl-1H-imidazol-4-ylethynyl)-pyridine

The title compound, MS: m/e=286.1 (M+H$^+$), was prepared in accordance with the general method of example 1 from 2-chloro-4-(2-methyl-1H-imidazol-4-ylethynyl)-pyridine and cydobutyl-methylbromide.

EXAMPLE 11

2-Methyl-4-[2-methyl-1-(2-phenoxy-ethyl)-1H-imidazol-4-ylethynyl]-pyridine

The title compound, MS: m/e=318.1 (M+H$^+$), was prepared in accordance with the general method of example 1 from 2-methyl-4-(2-methyl-1H-imidazol-4-ylethynyl)-pyridine and 2-phenoxyethyl bromide.

EXAMPLE 12

2-Chloro-4-(1,2-dimethyl-1H-imidazol-4-ylethynyl)-pyridine

The title compound, MS: m/e=232.1 (M+H$^+$), was prepared in accordance with the general method of example 1 from 2-chloro-4-(2-methyl-1H-imidazol-4-ylethynyl)-pyridine and methyl iodide.

EXAMPLE 13

4-(2-Cyclopropyl-1-methyl-1H-imidazol-4-ylethynyl)-2-methyl-pyridine

Step 1: 2-Cyclopropyl-4-iodo-1-methyl-1H-imidazole

The title compound, MS: m/e=249.1 (M+H$^+$), was prepared in accordance with the general method of example 1 from 2-cyclopropyl-5-iodo-1H-imidazole (example C) and iodomethane.

Step 2: 4-(2-Cyclopropyl-1-methyl-1H-imidazol-4-ylethynyl)-2-methyl-pyridine

The title compound, MS: m/e=238.1 (M+H$^+$), was prepared in accordance with the general method of example A, step 2 from 2-chloro-4-trimethylsilanylethynyl-pyridine and 2-cyclopropyl-4-iodo-1-methyl-1H-imidazole.

EXAMPLE 14

2-Chloro-4-(1-isopropyl-2-methyl-1H-imidazol-4-ylethynyl)-pyridine

The title compound, MS: m/e=260.6 (M+H+), was prepared in accordance with the general method of example 1 from 2-chloro-4-(2-methyl-1H-imidazol-4-ylethynyl)-pyridine and isopropylbromide.

EXAMPLE 15

4-(2-Cyclopropyl-1-isopropyl-1H-imidazol-4-ylethynyl)-2-methyl-pyridine

Step 1: 2-Cyclopropyl-4-iodo-1-isopropyl-1H-imidazole

The title compound, MS: m/e=277.1 (M+H$^+$), was prepared in accordance with the general method of example 1 from 2-cyclopropyl-5-iodo-1H-imidazole (example C) and isopropylbromide.

Step 2: 4-(2-Cyclopropyl-1-isopropyl-1H-imidazol-4-ylethynyl)-2-methyl-pyridine

The title compound, MS: m/e=266.3 (M+H+), was prepared in accordance with the general method of example A, step 2 from 2-methyl-4-trimethylsilanylethynyl-pyridine and 2-cyclopropyl-4-iodo-1-isopropyl-1H-imidazole.

EXAMPLE 16

4-(1-Cyclobutyl-2-methyl-1H-imidazol-4-ylethynyl)-2-methyl-pyridine

The title compound, MS: m/e=252.4 (M+H$^+$), was prepared in accordance with the general method of example 1 from 2-methyl-4-(2-methyl-1H-imidazol-4-ylethynyl)-pyridine and bromocyclobutane.

EXAMPLE 17

4-(1-Cyclopentyl-2-methyl-1H-imidazol-4-ylethynyl)-2-methyl-pyridine

The title compound, MS: m/e=266.3 (M+H$^+$), was prepared in accordance with the general method of example 1 from 2-methyl-4-(2-methyl-1H-imidazol-4-ylethynyl)-pyridine and bromocyclopentane.

EXAMPLE 18

4-[1-(2,2-Difluoro-ethyl)-2-methyl-1H-imidazol-4-ylethynyl]-2-methyl-pyridine The title compound, MS: m/e=262.1 (M+H$^+$), was prepared in accordance with the general method of example 1 from 2-methyl-4-(2-methyl-1H-imidazol-4-ylethynyl)-pyridine and 2-bromo-1,1-difluoro ethane.

EXAMPLE 19

2-Chloro-4-[1-(2,2-difluoro-ethyl)-2-methyl-1H-imidazol-4-ylethynyl]-pyridine Step 1: 1-(2,2-Difluoro-ethyl)-4-iodo-2-methyl-1H-imidazole The title compound, MS: m/e=273.0 (M+H+), was prepared in accordance with the general method of example 1 from 5-iodo-2-methyl-1H-imidazole and 2-bromo-1,1-difluoroethane.

Step 2: 2-Chloro-4-[1-(2,2-difluoro-ethyl)-2-methyl-1H-imidazol-4-ylethynyl]-pyridine The title compound, MS: m/e=282.0 (M+H+), was prepared in accordance with the general method of example A, step 2, from 2-chloro-4-trimethylsilanylethynyl-pyridine and 1-(2,2-difluoro-ethyl)-4-iodo-2-methyl-1H-imidazole.

EXAMPLE 20

4-[1-((E)-2-Fluoro-vinyl)-2-methyl-1H-imidazol-4-ylethynyl]-2-methyl-pyridine The title compound, MS: m/e=242.3 (M+H$^+$), was prepared in accordance with the general method of example 1 from 2-methyl-4-(2-methyl-1H-imidazol-4-ylethynyl)-pyridine and 2-bromo-1,1-difluoro ethane as a by-product.

EXAMPLE 21

2-Methyl-4-[2-methyl-1-(2,2,2-trifluoro-ethyl)-1H-imidazol-4-ylethynyl]-pyridine The title compound, MS: m/e=280.1 (M+H$^+$), was prepared in accordance with the general method of example 1 from 2-methyl-4-(2-methyl-1H-imidazol-4-ylethynyl)-pyridine and 2,2,2-trifluoroethyl mesylate.

EXAMPLE 22

2-Chloro-4-[2-methyl-1-(2,2,2-trifluoro-ethyl)-1H-imidazol-4-ylethynyl]-pyridine Step 1: 4-Iodo-2-methyl-1-(2,2,2-trifluoro-ethyl)-1H-imidazole The title compound, MS: m/e=291.0 (M+H+), was prepared in accordance with the general method of example 1 from 5-iodo-2-methyl-1H-imidazole and 2,2,2-trifluoroethyl mesylate.

Step 2: 2-Chloro-4-[2-methyl-1-(2,2,2-trifluoro-ethyl)-1H-imidazol-4-ylethynyl]-pyridine The title compound, MS: m/e=300.0 (M+H+), was prepared in accordance with the general method of example A, step 2, from 2-chloro-4-trimethylsilanylethynyl-pyridine and 4-iodo-2-methyl-1-(2,2,2-trifluoro-ethyl)-1H-imidazole.

EXAMPLE 23

2-Chloro-4-(1-cyclopropyl-2,5-dimethyl-1H-imidazol-4-ylethynyl)-pyridine

The title compound, MS: m/e=272.0 (M+H+), was prepared in accordance with the general method of example A, step 1 from 1-cyclopropyl-4-ethynyl-2,5-dimethyl-1H-imidazole and 2-chloro-4-iodo-pyridine.

EXAMPLE 24

4-(1-Cyclopropyl-2,5-dimethyl-1H-imidazol-4-ylethynyl)-2-methyl-pyridine

The title compound, MS: m/e=252.1 (M+H+), was prepared in accordance with the general method of example A, step 1 from 1-cyclopropyl-4-ethynyl-2,5-dimethyl-1H-imidazole and 4-iodo-2-methyl-pyridine.

Synthesis of Intermediates:

EXAMPLE A

2-Chloro-4-(2-methyl-1H-imidazol-4-ylethynyl)-pyridine

Step 1: 2-Chloro-4-trimethylsilanylethynyl-pyridine

2-Chloro-4-iodo-pyridine (10.0 g, 41.8 mmol) was dissolved in 200 mL of dry THF and 17.5 mL of triethyl amine. This mixture was evacuated and backfilled with argon several times to remove oxygen from the solution. Triphenylphosphine (329 mg, 1.25 mmol) and bis(triphenylphosphine)palladium(II)chloride (1.47 g, 2.09 mmol) were added and the reaction mixture was stirred at room temperature for 1 h. Copper(I)iodide (239 mg, 1.25 mmol) and trimethylsilylacetylene (6.28 g, 6.39 mmol) were added. The reaction mixture was stirred at room temperature overnight. The solvent was evaporated. The residue was taken up in 500 mL of water and extracted three times with ethyl acetate (500 mL each). The combined organic extracts were dried with magnesium sulfate, filtered and evaporated. The crude product was purified by chromatography on silica gel (cyclohexane/ethyl acetate 80:20). The desired product was obtained as a light brown semi solid (10 g,>100%). This material was used without any further purification for the next step.

Step 2: 2-Chloro-4-(2-methyl-1H-imidazol-4-ylethynyl)-pyridine

Solution 1: 2-Chloro-4-trimethylsilanylethynyl-pyridine (8.9 g, purity <100% as indicated in step 1) and 5-iodo-2-methyl-1H-imidazole (13.24 g, 64 mmol, synthesis: M. D. Cliff, S. G. Pyne, *Synthesis* 1994, 681–682) were dissolved in 75 mL of dry THF and 20 mL of dry DMF. This mixture was evacuated and backfilled with argon several times to remove oxygen from the solution.

Solution 2: Triphenylphosphine (223 mg, 0.85 mmol), bis(triphenylphosphine)-palladium(II)chloride (1.79 g, 2.55 mmol), copper(I)iodide (81 mg, 0.43 mmol) and triethyl amine (8.87 mL, 64 mmol) were dissolved in 75 mL of dry THF. This mixture was also evacuated and backfilled with argon several times to remove oxygen from the solution Solution 2 was heated to 40° C. and solution 1 was added dropwise. The reaction mixture was heated to 60° C. and tetrabutylammonium fluoride solution (1M in THF, 55 mL, 55 mmol) was added dropwise during 45 min. The reaction was than stirred at room temperature overnight. The solvent was evaporated. The residue was taken up in 200 mL of water and extracted three times with ethyl acetate (200 mL each). The combined organic extracts were dried with magnesium sulfate, filtered and evaporated. The crude product was purified by chromatography on silica gel (methylene chloride/methanol 95:5) and recrystallized from a mixture of methylene chloride and ethyl acetate. The desired product was obtained as a light brown solid (2.89 g, 31%).

EXAMPLE B

2-Methyl-4-(2-methyl-1H-imidazol-4-ylethynyl)-pyridine

The title compound was prepared in accordance with the general method of example A (step 1 and 2) from 4-iodo-2-methyl-pyridine and 5-iodo-2-methyl-1H-imidazole.

EXAMPLE C

2-Cyclopropyl-5-iodo-1H-imidazole

Step 1: 2-Cyclopropyl-1H-imidazole

The title compound can be prepared in accordance with patent WO 2002060877.

Step 2: 2-Cyclopropyl-5-iodo-1H-imidazole

The title compound was prepared in accordance with the literature reference of Cliff & Pyne, Synthesis-Stuttgart (7), 681–682(1994) by reacting 2-cyclopropyl-1H-imidazole with iodine in the presence of NaOH. The obtained 4,5-diiodo-2-cyclopropyl-1H-imidazole was then reacted with sodium sulfite to obtain the title compound.

EXAMPLE D

1-Cyclopropyl-4-ethynyl-2,5-dimethyl-1H-imidazole

Step 1: 4-[1-Dimethylamino-eth-(Z)-ylidene]-2-methyl-4H-oxazol-5-one

N-Acetylglycine (40.0 g, 342 mmol) and phosphoroxychloride (79.0 ml, 854 mmol) were mixed and cooled to 5° C. N,N'-Dimethylacetamide (80.0 ml, 854 mmol) was added drop-wise slowly during 30 min at 5–10° C. (exothermic!). The reaction mixture was stirred at 45° C. for 2.5 hrs and then cooled to room temperature. Dichloromethane (150 ml) was added and the mixture poured into 800 ml of ice-water. The pH was adjusted to pH 8 with ammonium hydroxide and the mixture was extracted twice with 200 ml of dichloromethane. The organic extracts were washed with 150 ml of water, dried over magnesium sulfate, filtered and evaporated. The crude product was purified by column chromatography on silica gel (ethyl acetate) and the desired compound was obtained as an orange solid (12.5 g, 22%), MS: m/e=169.2 (M+H$^+$).

Step 2: (Z)-2-Acetylamino-3-dimethylamino-but-2-enoic acid ethyl ester

4-[1-Dimethylamino-eth-(Z)-ylidene]-2-methyl-4H-oxazol-5-one (36.4 g, 216 mmol) was dissolved in ethanol (300 ml) and sodium hydride (0.52 g, 0.022 mmol) was added at room temperature. The dark solution was refluxed for 1 h. The solvent was evaporated and the crude product [MS: m/e=215.5 (M+H+)] was used without any further purification for the next step.

Step 3: (Z)-2-Acetylamino-3-cyclopropylamino-but-2-enoic acid ethyl ester (Z)-2-Acetylamino-3-dimethylamino-but-2-enoic acid ethyl ester (4.3 g, 20 mmol) and cyclopropylamine (1.14 g, 20 mmol) were stirred at room temperature in acetic acid (40 ml) for 2 hrs. The reaction mixture was diluted slowly with 30 ml of water and evaporated under vacuum at 35° C. Water (30 ml) was added to the residue and evaporated again at 35° C. The same procedure was repeated twice with toluene (30 ml each) to obtain the desired crude product as a dark brown oil [MS: m/e=227.4 (M+H$^+$)], which could be used without any further purification for the next step.

Step 4: 1-Cyclopropyl-2,5-dimethyl-1H-imidazole-4-carboxylic acid ethyl ester

Fine powdered ammonium sulfate (0.13 g, 1 mmol) was added to a suspension of Z)-2-acetylamino-3-cyclopropylamino-but-2-enoic acid ethyl ester (7.0 g, 20 mmol) and hexamethyldisilazane (50 ml, 235 mmol) and refluxed over night at 145° C. The reaction mixture was evaporated and extracted with ethyl acetate and water. The organic phase was dried over sodium sulfate and evaporated. The crude product was purified by column chromatography on silica gel (ethyl acetate/methanol 4:1) and the desired compound was obtained as a light brown solid (1.3 g, 31%), MS: m/e=209.1 (M+H+).

Step 5: (1-Cyclopropyl-2,5-dimethyl-1H-imidazol-4-yl)-methanol

Cyclopropyl-2,5-dimethyl-1H-imidazole-4-carboxylic acid ethyl ester (0.7 g, 3 mmol) was dissolved in 20 mL dry THF and cooled to 0° C. Lithium aluminum hydride (3.4 mL, 1M in THF, 3 mmol) was added dropwise and stirred for 1 h at 0° C. The reaction mixture was quenched with 0.13 ml of water, 0.13 ml of 4N sodium hydroxide and 0.4 ml of water. Sodium sulfate was added, stirred for 10 min, filtered and evaporated to dryness to obtain the desired compound as a light yellow solid (0.52 g, 93%), MS: m/e=167.4 (M+H)$^+$.

Step 6: 1-Cyclopropyl-2,5-dimethyl-1H-imidazole-4-carbaldehyde

Cyclopropyl-2,5-dimethyl-1H-imidazol-4-yl)-methanol (0.52 g, 3 mmol) was dissolved in 60 ml of dichloromethane. Mangan (IV) oxid (3 g, 30 mmol) was added and the reaction mixture stirred at reflux for 2 hrs. The suspension was filtered through a dicalite speed plus pad and washed with dichloromethane. The solvents were evaporated and the desired compound was obtained as a brown solid (0.42 g, 82%), MS: m/e=165.3 (M+H⁺).

Step 7: 1-Cyclopropyl-4-ethynyl-2,5-dimethyl-1H-imidazole

Diazo-2-oxo-propyl)-phosphonic acid dimethyl ester (0.6 g, 3 mmol) was dissolved in 10 mL of methanol. Potassium carbonate (0.74 g, 5 mmol) was added. A solution of 1-Cyclopropyl-2,5-dimethyl-1H-imidazole-4-carbaldehyde (0.42 g, 3 mmol) in 5 ml methanol was added drop wise at room temperature. The reaction mixture was stirred at room temperature overnight. The solvent was evaporated. The residue was taken up in 15 mL water and extracted three times with ethyl acetate (15 ml each). The combined organic extracts were dried with sodium sulfate, filtered and evaporated. The crude product was purified by flash chromatography on silica gel (heptane/ethyl acetate 80:20→0:100 gradient) and the desired compound was obtained as a white solid (0.12 g, 30%), MS: m/e=161.4 (M+).

Preparation of the Pharmaceutical Compositions:

EXAMPLE I

Tablets of the following composition are produced in a conventional manner:

|  | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets of the following composition are produced in a conventional manner:

|  | mg/Tablet |
| --- | --- |
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula I

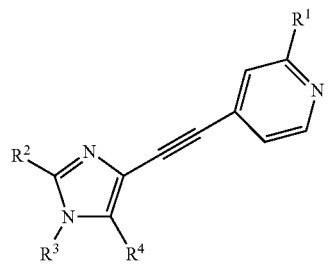

wherein
  $R^1$ is selected from halogen, lower alkyl, lower alkoxy, $CF_3$, $CF_2H$, $OCF_3$, $OCF_2H$, and cyano;
  $R^2$ is lower alkyl or cycloalkyl;
  $R^3$ is selected from lower alkyl, cycloalkyl, —$(CH_2)_n$-cycloalkyl, —$(CH_2)_n$—CN, —$(CH_2)_n$—O-lower alkyl, lower-alkyleneoxy aryl, and —$R^5$—$F_n$ wherein $R^5$ is lower alkyl or lower alkenyl; and n is 1, 2 or 3; and
  $R^4$ is selected from hydrogen, C(O)H, and $CH_2R^5$, wherein $R^5$ is selected from hydrogen, OH, $C_1$–$C_6$-alkyl, and $C_3$–$C_{12}$-cycloalkyl;
or a pharmaceutically acceptable salt thereof.

2. The compound of formula I according to claim 1 wherein
  $R^1$ is selected from halogen and lower alkyl;
  $R^2$ is lower alkyl or cycloalkyl;
  $R^3$ is selected from lower alkyl, cycloalkyl, —$(CH_2)_n$-cycloalkyl, —$(CH_2)_n$—CN, —$(CH_2)_n$—O-lower alkyl, lower-alkyleneoxy aryl, and —$R^5$—$F_n$ wherein $R^5$ is lower alkyl or lower alkenyl; and n is 1, 2 or 3; and
  $R^4$ is selected from hydrogen and $CH_2R^5$, wherein $R^5$ is selected from hydrogen;
or a pharmaceutically acceptable salt thereof.

3. A compound of formula IA wherein
R$^1$ is selected from halogen, lower alkyl, lower alkoxy, CF$_3$, CF$_2$H, OCF$_3$, OCF$_2$H, and cyano;
R$^2$ is lower alkyl or cycloalkyl; and
R$^3$ is selected from lower alkyl, cycloalkyl, —(CH$_2$)$_n$-cycloalkyl, —(CH$_2$)$_n$—CN, —(CH$_2$)$_n$—O-lower alkyl, lower-alkyleneoxy aryl, and —R$^5$—F$_n$ wherein R$^5$ is lower alkyl or lower alkenyl; and n is 1, 2 or 3;
or a pharmaceutically acceptable salt thereof.

4. The compound according to claim 3 wherein
R$^1$ is selected from halogen and lower alkyl;
R$^2$ is lower alkyl or cycloalkyl; and
R$^3$ is selected from lower alkyl, cycloalkyl, —(CH$_2$)$_n$-cycloalkyl, —(CH$_2$)$_n$—CN, —(CH$_2$)$_n$—O-lower alkyl, lower-alkyleneoxy aryl, and —R$^5$—F$_n$ wherein R$^5$ is lower alkyl or lower alkenyl; and n is 1, 2 or 3;
or a pharmaceutically acceptable salt thereof.

5. The compound of formula I in accordance with claim 1, wherein R$^3$ is —CH$_2$-cycloalkyl.

6. The compound of formula I in accordance with claim 5, wherein the compound is selected from
4-(1-cyclopropylmethyl-2-methyl-1H-imidazol-4-ylethynyl)-2-methyl-pyridine,
4-(1-cyclobutylmethyl-2-methyl-1H-imidazol-4-ylethynyl)-2-methyl-pyridine,
2-chloro-4-(1-cyclopropylmethyl-2-methyl-1H-imidazol-4-ylethynyl)-pyridine and
2-chloro-4-(1-cyclobutylmethyl-2-methyl-1H-imidazol-4-ylethynyl)-pyridine.

7. The compound of formula I in accordance with claim 1, wherein R$^3$ is lower alkyl.

8. The compound of formula I in accordance with claim 7, wherein the compound is selected from
4-(1,2-dimethyl-1H-imidazol-4-ylethynyl)-2-methyl-pyridine,
4-(1-isopropyl-2-methyl-1H-imidazol-4-ylethynyl)-2-methyl-pyridine,
4-(1-isobutyl-2-methyl-1H-imidazol-4-ylethynyl)-2-methyl-pyridine and
2-chloro-4-(1-isobutyl-2-methyl-1H-imidazol-4-ylethynyl)-pyridine.

9. The compound of formula I in accordance with claim 1, wherein R$^3$ is selected from
—CH$_2$—CN and —(CH$_2$)$_2$—O-lower alkyl.

10. The compound of formula I in accordance with claim 9, wherein the compound is selected from
[2-methyl-5-(2-methyl-pyridin-4-ylethynyl)-imidazol-1-yl]-acetonitrile and
4-[1-(2-methoxy-ethyl)-2-methyl-1H-imidazol-4-ylethynyl]-2-methyl-pyridine.

11. A pharmaceutical composition which comprises a compound of formula I

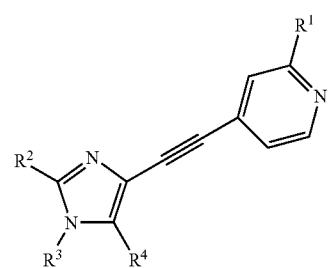

wherein
R$^1$ is selected from halogen, lower alkyl, lower alkoxy, CF$_3$, CF$_2$H, OCF$_3$, OCF$_2$H, and cyano;
R$^2$ is lower alkyl or cycloalkyl;
R$^3$ is selected from lower alkyl, cycloalkyl, —(CH$_2$)$_n$-cycloalkyl, —(CH$_2$)$_n$—CN, —(CH$_2$)$_n$—O-lower alkyl, lower-alkyleneoxy aryl, and —R$^5$—F$_n$ wherein R$^5$ is lower alkyl or lower alkenyl; and n is 1, 2 or 3; and
R$^4$ is selected from hydrogen, C(O)H, and CH$_2$R$^5$, wherein R$^5$ is selected from hydrogen, OH, C$_1$–C$_6$-alkyl, and C$_3$–C$_{12}$-cycloalkyl;
or a pharmaceutically acceptable salt thereof; and a pharmaceutical acceptable carrier.

* * * * *